(12) United States Patent
Takeuchi et al.

(10) Patent No.: US 12,153,036 B2
(45) Date of Patent: Nov. 26, 2024

(54) ESTIMATION METHOD

(71) Applicant: Nippon Telegraph and Telephone Corporation, Tokyo (JP)

(72) Inventors: Yosuke Takeuchi, Musashino (JP); Takuya Kamisho, Musashino (JP); Masayuki Tsuda, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 474 days.

(21) Appl. No.: 17/431,571

(22) PCT Filed: Feb. 6, 2020

(86) PCT No.: PCT/JP2020/004448
§ 371 (c)(1),
(2) Date: Aug. 17, 2021

(87) PCT Pub. No.: WO2020/170829
PCT Pub. Date: Aug. 27, 2020

(65) Prior Publication Data
US 2022/0137022 A1     May 5, 2022

(30) Foreign Application Priority Data

Feb. 20, 2019   (JP) .................................. 2019-028305

(51) Int. Cl.
*G01N 33/2045*    (2019.01)
*G01N 17/00*    (2006.01)

(52) U.S. Cl.
CPC ....... *G01N 33/2045* (2019.01); *G01N 17/006* (2013.01)

(58) Field of Classification Search
CPC .......................... G01N 33/2045; G01N 17/006
(Continued)

(56) References Cited

U.S. PATENT DOCUMENTS

| 5,817,958 A | * | 10/1998 | Uchida | .................... G21D 3/04 376/217 |
| 2002/0111749 A1 | * | 8/2002 | Yang | ........................ G01B 3/44 702/34 |
| 2005/0028882 A1 | * | 2/2005 | Wada | ................. G01N 33/2045 138/146 |

FOREIGN PATENT DOCUMENTS

| JP | 2002365202 A | * | 12/2002 |
| JP | 2012159486 A | * | 8/2012 |

OTHER PUBLICATIONS

English translation for JP-2002365202-A (Year: 2002).*

(Continued)

*Primary Examiner* — Lee E Rodak
*Assistant Examiner* — Byung Ro Lee
(74) *Attorney, Agent, or Firm* — Workman Nydegger (57) ABSTRACT

To improve the accuracy of estimating when a fracture occurred in the metal material. In the estimation apparatus, the fracture temperature estimation unit performs estimate calculation of the fracture temperature of a fractured metal material from the hydrogen embrittlement rate of the fractured metal material, the fracture occurrence time narrowing unit performs calculation by using the temperature information of the installation environment in which the fractured metal material is installed and narrow down the period during which the fracture temperature is obtained as the fracture occurrence period of the metal material, and the fracture time estimation unit performs estimate calculation of the timing of when stress was applied to the fractured metal material during the fracture occurrence period as the timing of when a fracture occurred in the metal material.

11 Claims, 7 Drawing Sheets

(58) Field of Classification Search
USPC .......................................................... 702/34
See application file for complete search history.

(56) References Cited

OTHER PUBLICATIONS

English translation for JP-2012159468-A (Year: 2012).*
XiaoXing, Quantification of Temperature Dependence of Hydrogen Embrittlement in Pipeline Steel, Materials 2019, 12, 585 (Year: 2019).*
Eiji Akiyama, *Hydrogen Embrittlement of Metallic Materials and Recent Subjects*, Materia, vol. 56, No. 3, 2017, pp. 230-233.
Michihiko Nagumo, *Fracture Process of Hydrogen Embrittlement~Mechanism of Hydrogen Embrittlement~*, Pressure Technology, vol. 46, No. 4, 2018, pp. 190-199.
Susumu Matsuyama, *Delayed Destruction*, Nikkan Kogyo Shimbun, 1989, p. 97.

\* cited by examiner

ESTIMATION METHOD

TECHNICAL FIELD

The present invention relates to a technique for estimating when a fracture occurred in a metal material.

BACKGROUND ART

Breakage (fracture) of a metal material due to hydrogen embrittlement is a fracture mode that is difficult to predict, as it is also called delayed fracture, and is an event that reveals that the cause of breakage was hydrogen embrittlement after breakage. Further, it is difficult to grasp the deterioration process of a metal material due to hydrogen embrittlement (Non Patent Literature 1).

As a countermeasure against hydrogen embrittlement of the metal material, preventive measures for preventing the metal material from being exposed to the environment where hydrogen embrittlement occurs are effective. On the other hand, if the metal material must be exposed to an environment that causes hydrogen embrittlement, it is desirable to renew the material before hydrogen embrittlement occurs. At this time, in order to renew the metal material, it is necessary to know the service period until the metal material causes hydrogen embrittlement in the service environment. The service period is confirmed by investigating the period since the metal material is actually put into service until the metal material is broken by hydrogen embrittlement. In general, the service period is confirmed by checking at predetermined time intervals whether or not the material is broken due to hydrogen embrittlement.

CITATION LIST

Non Patent Literature

[Non Patent Literature 1] Akiyama, "Hydrogen Embrittlement of Metal Materials and Recent Subjects", Materia, Vol. 56, No. 3, 2017, pp. 230-233
[Non Patent Literature 2] Nagumo, "Fracture Process of Hydrogen Embrittlement-Mechanism of Hydrogen Embrittlement-", Pressure Engineering, JHPI, Vol. 46, No. 4, 2018, pp. 190-199
[Non Patent Literature 3] Matsuyama, "Delayed Breakage", 1989, p. 97

SUMMARY OF THE INVENTION

Technical Problem

However, when checking the period until breakage due to hydrogen embrittlement by regular inspection work, the detailed timing of the fracture during the inspection interval is unknown, and the inspection interval is the minimum unit of the service period. Therefore, it is difficult to evaluate correctly when the fracture occurred. Further, a method of constantly monitoring a metal material using a strain sensor or the like is possible, but the introduction and maintenance of the sensor is costly.

The present invention has been made in view of the above circumstances, and an object of the present invention is to improve the accuracy of estimating when a fracture occurred in a metal material.

Means for Solving the Problem

In order to solve the above problems, the estimation method of the present invention is an estimation method for estimating when a fracture occurred in a metal material, the method performed by an estimation apparatus, the method including: (i) calculating a fracture temperature of a fractured metal material from a hydrogen embrittlement rate of the fractured metal material; (ii) calculating the period during which the fracture temperature was obtained as a fracture occurrence period of the fractured metal material by using temperature information of an installation environment in which the fractured metal material was installed; and (iii) calculating a timing of when stress was applied to the fractured metal material during the fracture occurrence period as a timing of when a fracture occurred in the fractured metal material.

In the estimation method, the hydrogen embrittlement rate is a percentage brittle fracture indicating a ratio of a hydrogen embrittlement fracture surface to an entire fracture surface in a fracture surface of the fractured metal material, on assumption that a fracture surface including dimples is a ductile fracture surface and a fracture surface other than the fracture surface including dimples is a hydrogen embrittlement fracture surface, and in the step (i), a relational expression depicting a relationship between the percentage brittle fracture and the fracture temperature in the fractured metal material is used.

In the estimation method, the hydrogen embrittlement rate is the ratio of a reduction of area of the fractured metal material which fractured in air to a reduction of area of the fractured metal material which fractured in hydrogen, and in the step (i), a relational expression depicting a relationship between the ratio and the fracture temperature in the fractured metal material.

In the estimation method, in the step (iii), outliers of the stress applied during the fracture occurrence period are detected using a predetermined outlier test method, and a period during which outliers are continuously detected is calculated on the assumption that a longer period during which outliers are continuously detected is a period when higher stress was applied.

In the estimation method, the fractured metal material is a metal material installed outdoors or a metal material contained in a structure installed outdoors, and in the step (iii), outliers of outdoor wind power loaded during the fracture occurrence period are detected using a predetermined outlier test method, and a period during which outliers are continuously detected is calculated on the assumption that a longer period during which outliers are continuously detected is a period when larger wind was applied.

In the estimation method, in the step (iii), periods during which outliers are continuously detected are ranked in descending order of period length on the assumption that a longer period during which outliers are continuously detected is a period when higher stress was applied, and the timing of when a fracture occurred in the fractured metal material is also ranked according to the ranking of the periods during which outliers are continuously detected.

In the estimation method, in the step (iii), periods during which outliers are continuously detected are ranked in descending order of period length on the assumption that a longer period during which outliers are continuously detected is a period when larger wind was applied.

In the estimation method, the fractured metal material is a steel material contained in a concrete structure.

In the estimation method, the structure is a concrete pole.

Effects of the Invention

According to the present invention, the accuracy of estimating when a fracture occurred in a metal material can be improved.

DESCRIPTION OF EMBODIMENTS

Hereinafter, an embodiment of the present invention will be described with reference to the drawings.

Overview

An object of the present embodiment is to estimate when a break (fracture) occurred in a metal material fractured due to hydrogen embrittlement. Information on hydrogen embrittlement obtained from a metal material broken (fractured) due to hydrogen embrittlement includes, for example, fracture surface morphology and reduction of area. Therefore, for example, when the fracture surface morphology is used, the estimate calculation of the temperature at the timing of fracturing is performed from the percentage brittle fracture in the entire fracture surface by taking advantage of the fact that the fracture surface morphology changes depending on the temperature at the timing of fracturing. Then, by applying the outcome (temperature condition) of the estimate calculation of the temperature at the timing of fracturing to the temperature information of the installation environment, the period during which the breakage occurred is narrowed down from within the predetermined inspection interval. When it is clear when the high stress (stress condition) occurred, the stress condition is used to further narrow down the timing of when the breakage occurred. As a result, the accuracy of estimating when the fracture occurred in the metal material fractured due to hydrogen embrittlement is improved.

Configuration

Figure 1:
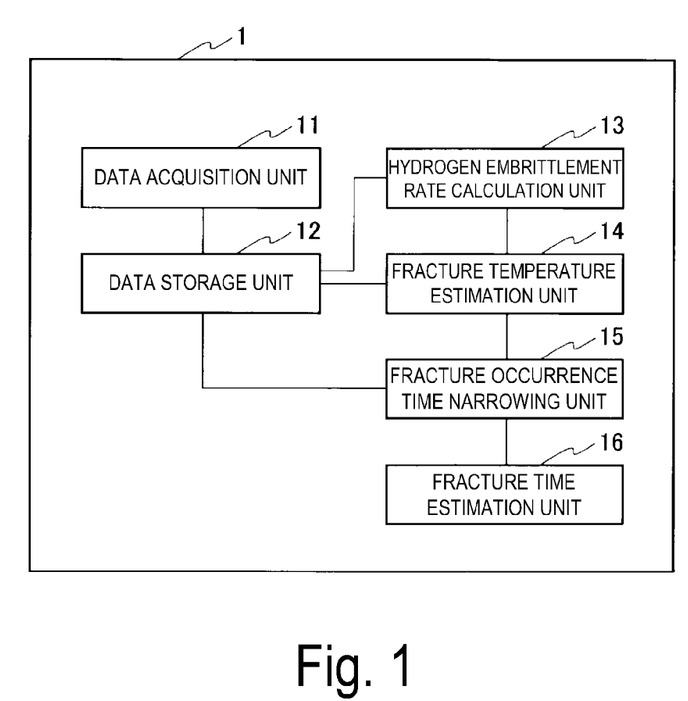
FIG. 1 is a diagram illustrating a configuration example of a functional block of an estimation apparatus.

In the present embodiment, an estimation apparatus 1 illustrated in FIG. 1 is used to estimate the timing of breakage in the metal material fractured due to hydrogen embrittlement. FIG. 1 is a diagram illustrating a configuration example of a functional block of the estimation apparatus 1. The estimation apparatus 1 mainly includes a data acquisition unit 11, a data storage unit 12, a hydrogen embrittlement rate calculation unit 13, a fracture temperature estimation unit 14, a fracture occurrence time narrowing unit 15, and a fracture timing estimation unit 16.

The data acquisition unit 11 has a function of acquiring data used for estimating when the metal material fractured.

The data acquisition unit 11 receives input such as the image data of a fracture surface of a metal material, fracture temperature of a metal material, image data of a fracture surface of a metal material fractured in air, image data of a fracture surface of a metal material fractured in hydrogen, temperature information of the installation environment where the metal material to be estimated was installed, and wind information (stress information) loaded on the metal material to be estimated.

The data storage unit 12 has a function of storing the data acquired by the data acquisition unit 11 in a readable manner.

The hydrogen embrittlement rate calculation unit 13 has a function of calculating the hydrogen embrittlement rate of the fractured metal material to be estimated. The hydrogen embrittlement rate is calculated based on, for example, the fracture surface morphology and the reduction of area. When calculating based on the fracture surface morphology, the hydrogen embrittlement rate calculation unit 13 obtains a hydrogen embrittlement rate as the outcome of calculating the percentage brittle fracture that indicates the ratio of the hydrogen embrittlement fracture surface to the entire fracture surface, on the assumption that, in the fracture surface of fractured metal material, the fracture surface including the dimples is the ductile fracture surface, and the fracture surface other than the fracture surface including the dimples is the hydrogen embrittlement fracture surface. When calculating based on the reduction of area, the hydrogen embrittlement rate calculation unit 13 obtains a hydrogen embrittlement rate as the outcome of calculating the ratio of the reduction of area of a metal material fractured in air to the reduction of area of the metal material fractured in hydrogen. The percentage brittle fracture or the reduction of area is calculated using the image data of the data storage unit 12.

The hydrogen embrittlement rate calculation unit 13 has a function of plotting the hydrogen embrittlement rate of the fractured metal material and the fracture temperature of the fractured metal material on the "hydrogen embrittlement rate-temperature graph", and deriving a relational expression F showing the relationship between the hydrogen embrittlement rate and the fracture temperature. When the hydrogen embrittlement rate is calculated based on the fracture surface morphology, the hydrogen embrittlement rate calculation unit 13 derives the relational expression F1 showing the relationship between the percentage brittle fracture and the fracture temperature. When the hydrogen embrittlement rate is calculated based on the reduction of area, the hydrogen embrittlement rate calculation unit 13 derives the relational expression F2 showing the relationship between the ratio of the reduction of area and the fracture temperature.

The fracture temperature estimation unit 14 has a function of performing estimate calculation of the fracture temperature K of the fractured metal material to be estimated from the hydrogen embrittlement rate of the metal material to be estimated using the derived relational expression F (F1, F2).

The fracture occurrence time narrowing unit 15 has a function of reading the temperature information of the installation environment in which the metal material to be estimated was installed from the data storage unit 12, and performing calculation by using the temperature information to narrow down the period T during which the estimate calculated fracture temperature K was obtained as the fracture occurrence period T of the metal material to be estimated.

The fracture time estimation unit 16 has a function of reading wind information (stress information) loaded on the metal material to be estimated from the data storage unit 12, and performing estimate calculation, using the wind information, of when a large wind force (high stress) is applied to the metal material to be estimated during the fracture occurrence period T which was narrowed down by the calculation. The estimate calculation outcome is assumed to be the timing of when the fracture occurred in the metal material to be estimated.

The fracture time estimation unit 16 has a function of detecting outliers of wind power (stress) applied during the fracture occurrence period T by using a predetermined outlier test method, and calculating the period in which outliers are continuously detected. The longer the calculated period is, the calculated period is assumed to be a timing of when larger wind force (higher stress) was applied.

The fracture time estimation unit 16 also has a function of ranking the timing of when a large wind force (high stress) was applied in descending order of the length of the period in which outliers are continuously detected, and ranking the timing of when fracture occurred according to the applied wind force ranking.

The metal material is installed indoors or outdoors, regardless of whether the metal material is inside or outside the structure (whether or not the metal material is exposed). Examples include exposed metal materials, metal materials contained in structures such as concrete poles, steel materials and reinforcing bars contained in concrete structures, plated steel materials, and painted steel materials installed indoors and outdoors. In general, indoor means the inside of a building (inside the school, government building, etc.), and outdoor means outside the building (road, ground, etc.). The metal material is not necessarily limited to either indoors or outdoors, and may be a steel material in concrete or the like that supports the roof of a ball game field, or a steel material in which both outdoors and indoors coexist.

Estimation Method

Figure 2:
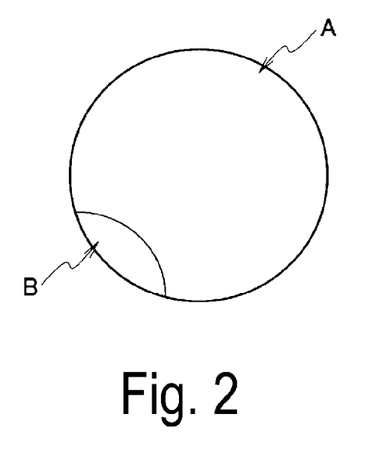
FIG. 2 is a diagram schematically illustrating a fracture surface (fractured surface) of a metal material.

Next, the method for estimating when a fracture occurred will be described in detail. In this estimation method, a case of estimating based on the fracture surface morphology will be described as an example. FIG. 2 illustrates a schematic view of the fracture surface morphology when a metal material such as a reinforcing bar is broken due to hydrogen embrittlement. The fracture surface of the metal material due to hydrogen embrittlement has various patterns and shapes depending on the conditions such as the grain boundary face and the quasi-cleavage fracture surface. As the ductile fracture surface, dimples are observed at the time of feature (Non Patent Literature 2).

Therefore, in the present embodiment, as shown in FIG. 2, the fracture surface A in which dimples are observed is regarded as a ductile fracture surface, and the fracture surface B other than the fracture surface in which dimples are observed is regarded as a hydrogen embrittlement fracture surface due to hydrogen embrittlement. Then, the percentage brittle fracture is calculated by dividing the area of the hydrogen embrittlement fracture surface (fracture surface B) by the area of the entire fracture surface (fracture surface A+fracture surface B).

Figure 3:
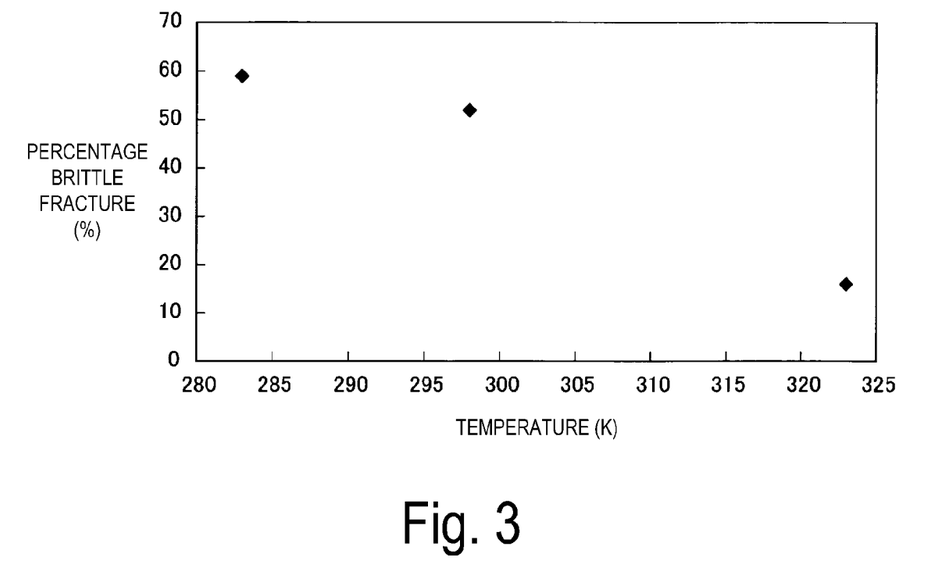
FIG. 3 is a graph showing the relationship between temperature and percentage brittle fracture in a metal material.

FIG. 3 shows an example in which the percentage brittle fracture and the fracture temperature of a metal material are plotted on a "hydrogen embrittlement rate-temperature graph". FIG. 3 illustrates the test result of the D-type metal material defined by "JISG 3137", in which a constant load of 994 MPa was applied to the metal material, then hydrogen was added by the cathode charge method, and the metal material was tested until fracture in contact with three different temperature solutions of 10° C., 25° C., and 50° C. As indicated in FIG. 3, the higher the temperature, the lower the percentage brittle fracture.

Figure 4:
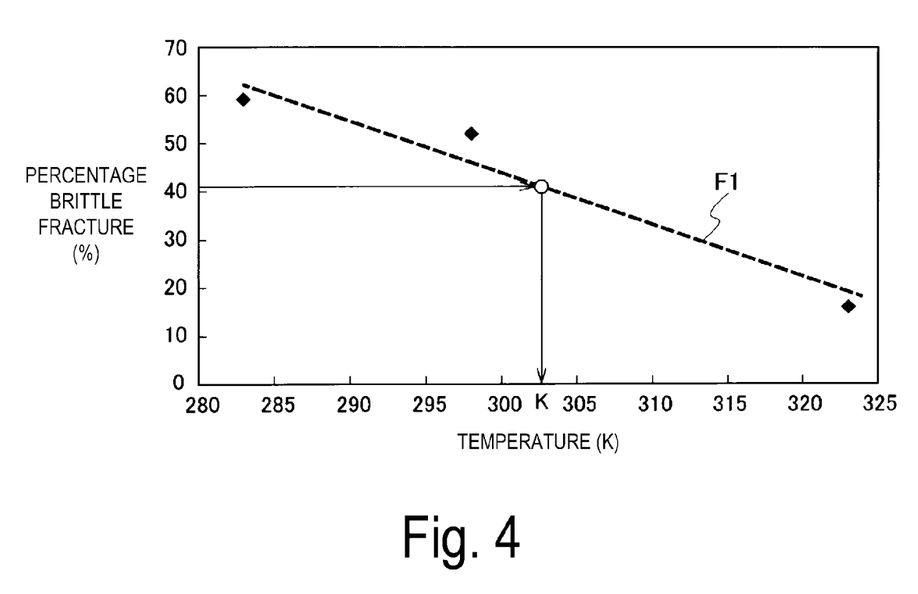
FIG. 4 is a graph showing an estimation example of a fracture temperature of a metal material.

Then, for the plot points of the "hydrogen embrittlement-temperature graph", for example, by obtaining an approximate expression by the least squares method, the relational expression F1 between the temperature and the percentage brittle fracture is derived as illustrated in FIG. 4. By substituting the percentage brittle fracture of the metal material to be estimated broken in the service environment into this relational expression F1, the fracture temperature K at the time of fracture is estimated and calculated as illustrated in FIG. 4.

Figure 5:
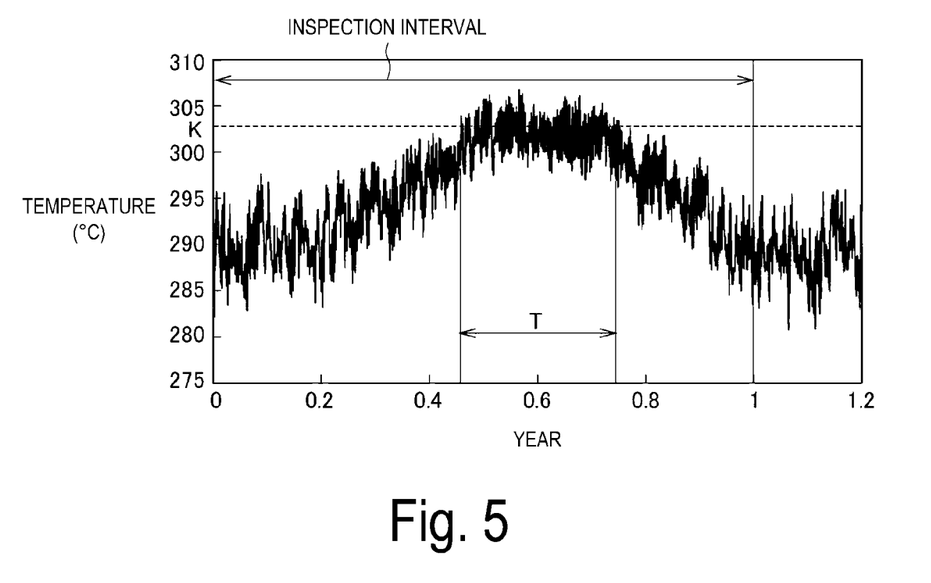
FIG. 5 is a graph showing an estimation example of a period during which a fracture occurred in a metal material.

After that, when the temperature change in the service environment is clear, the fracture occurrence period T at which the fracture occurs may be estimated and calculated from the estimated fracture temperature K. FIG. 5 illustrates the estimation result of the fracture occurrence period T in the case where the inspection interval is one year, the temperature change in the service environment is clear, and the fracture temperature K is estimated to be about 303° C. Since the period T having the condition that the fracture temperature K=303° C. was from 0.45 to 0.74 years in the transition of the temperature in the service environment, the fracture occurrence period T can be narrowed down from the inspection interval of 1 year to a shorter period of 0.29 years.

Furthermore, since metals are easily hydrogen-embrittled under high stress conditions (Non Patent Literature 3), when the conditions under which high stress is applied to the metal material to be estimated are clear, the time when the fracture occurs with high probability can be further narrowed down. For example, in an outdoor structure, stress is considered to be applied by wind pressure. Therefore, when the wind speed information in the service environment was acquired and the time when the wind speed was particularly high continued, it is presumed that the fracture occurred with a high probability. As a method for deriving the time when the wind speed is specifically high, that is, when the stress is particularly high, a predetermined outlier test method, for example, the Smirnov-Grabs test or the Thompson test is used. Then, it is estimated that the outlier evaluation by the test is detected in the continuous time with respect to the measurement result, and the hydrogen embrittlement fracture occurs with high probability in the descending order of the continuous time.

Figure 6:
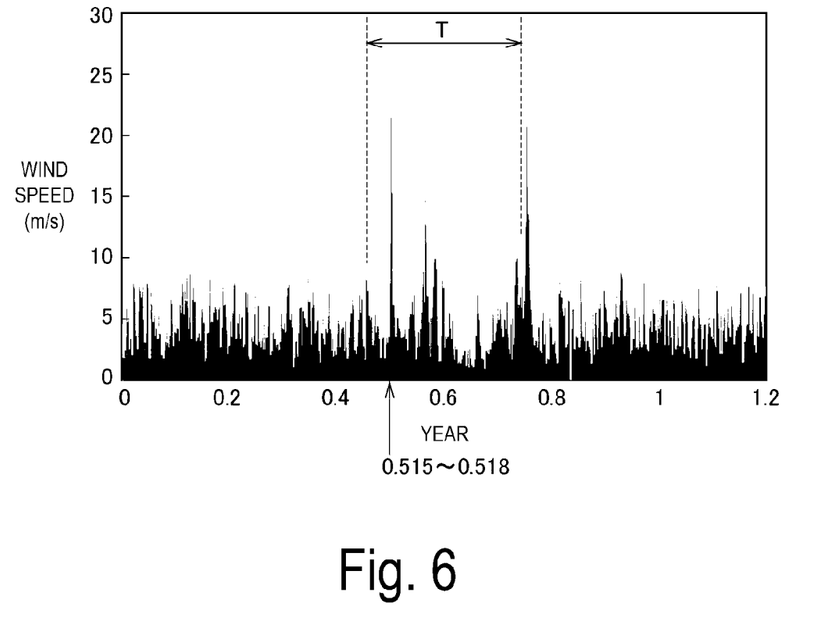
FIG. 6 is a graph showing an estimation example of when a fracture occurred in a metal material.

The measured value of the wind speed generated in the same period as the period in FIG. 5 is given in FIG. 6. In the fracture occurrence period T estimated from the fracture temperature K, when the wind speed outliers were tested, the longest duration of high stress conditions was from 0.515 to 0.518 years, or 32 hours, so that it can be estimated that the probability of fracture is highest when about 0.518 years have passed since the last inspection. Subsequently, the period with the second longest continuous time is evaluated as the second place. This estimation method can be combined even when the load stress on the metal material is measured with a strain gauge or the like under high stress conditions, and the ranking may be performed using outliers.

Figure 7:
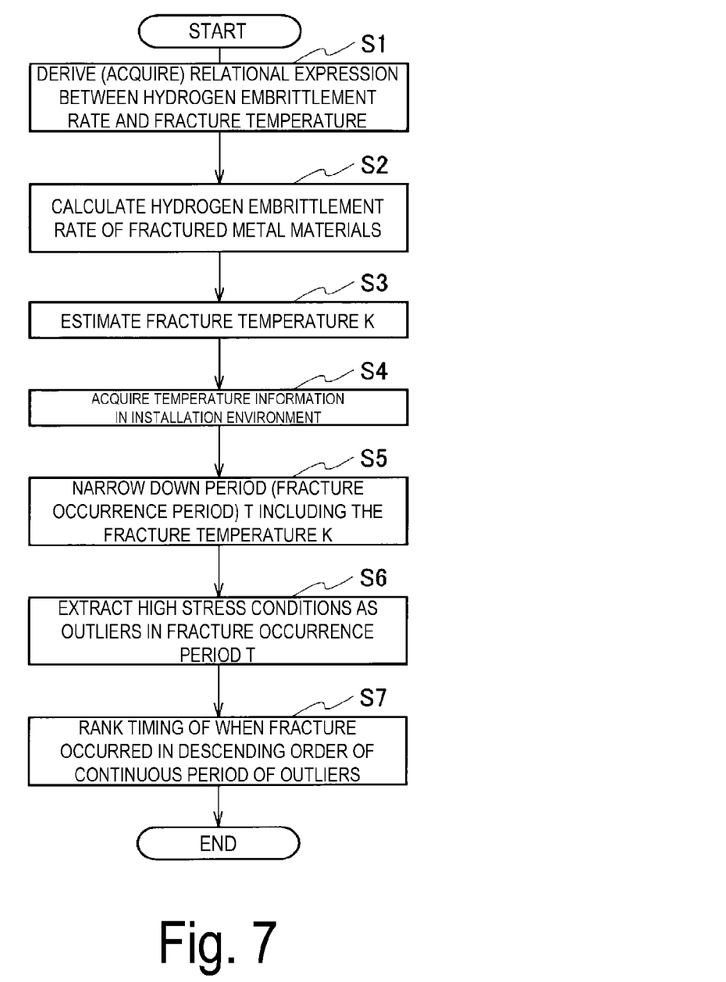
FIG. 7 is a flowchart illustrating a method for estimating when a fracture occurred in a metal material.

Finally, the estimation flow of the method for estimating the fracture time of the metal material performed by the estimation apparatus 1 will be described. FIG. 7 is a flowchart illustrating the estimation method.

Step S1

First, the hydrogen embrittlement rate calculation unit 13 plots the percentage brittle fracture of the fractured metal material and the fracture temperature of the fractured metal material on a "hydrogen embrittlement rate-temperature graph", and obtains an approximate expression for the plot by the least squares method to derive a relational expression F1 showing the relationship between the percentage brittle fracture and the fracture temperature (see FIG. 4). The hydrogen embrittlement rate calculation unit 13 may derive the relational expression F1 in advance and store it in the data storage unit 12.

Step S2

Next, the hydrogen embrittlement rate calculation unit 13 calculates the hydrogen embrittlement rate of the metal material to be estimated, using the image data of the fracture surface of the fractured metal material to be estimated. For example, the hydrogen embrittlement rate calculation unit 13 calculates the percentage brittle fracture, which indicates the ratio of the hydrogen embrittlement fracture surface to the entire fracture surface, by regarding the fracture surface A including the dimples as a ductile fracture surface and the fracture surface B other than the fracture surface including the dimples as the hydrogen embrittlement fracture surface in the fractured fracture surface of a metal material, thereby calculating the hydrogen embrittlement rate.

Step S3

Next, the fracture temperature estimation unit 14 substitutes the hydrogen embrittlement rate (percentage brittle fracture) calculated in step S2 into the relational expression F1 derived in step S1, thereby calculating the fracture temperature K of the metal material to be estimated (see FIG. 4).

Step S4

Next, the fracture occurrence time narrowing unit 15 acquires temperature information of the installation environment in which the metal material to be estimated is installed.

Step S5

Next, the fracture occurrence time narrowing unit 15 refers to the temperature information acquired in step S4, and narrows down the period T during which the estimated fracture temperature K was obtained from the inspection interval, for example, one year, as the fracture occurrence period T of the metal material to be estimated (see FIG. 5). As a result, the time when the fracture occurs can be narrowed down from the yearly unit to the monthly unit or the daily unit.

Step S6

Next, the fracture time estimation unit 16 refers to the information about the wind speed loaded on the metal material to be estimated, and performs estimate calculation of when a large wind speed is applied to the metal material to be estimated during the fracture occurrence period T which was narrowed down by the calculation and the estimate calculation outcome is assumed to be the timing of when the fracture occurred in the metal material to be estimated. For example, the fracture time estimation unit 16 uses the Smirnov-Grabs test method to detect an outlier, which is an extremely large wind speed among the wind speeds generated during the fracture occurrence period T, calculates the timing of when the larger wind speed is applied on assumption that a longer period during which outliers are continuously detected is a period when larger wind speed was applied, and determines when the fracture occurred in the metal material (see FIG. 6). As a result, the timing of when the fracture occurred can be further narrowed down from the monthly unit to the daily unit or the hour unit.

Step S7

Finally, the fracture time estimation unit 16 ranks the timing of when the large wind speed is applied in descending order on assumption that a longer period during which outliers are continuously detected is a period when higher wind speed was applied, also ranks the timing of when fracture occurred according to the applied wind speed ranking, and outputs the ranking results to a monitor or the like. In the case of the wind speed information shown in FIG. 6, the timing of when fracture occurred is displayed with 0.518 years after the previous inspection as the first place, 0.561 years after as the second place, and 0.732 years after as the third place of the fracture time.

Up to this point, in the present estimation method, the case of estimating based on the fracture surface morphology has been described as an example, but instead of the fracture surface morphology, the estimation may be performed based on the reduction of area. In that case, the hydrogen embrittlement rate calculation unit 13 calculates the ratio of the reduction of area of the metal material fractured in air to the reduction of area of the metal material fractured in hydrogen in step S2, thereby calculating the hydrogen embrittlement rate.

Advantages

Normally, the timing of when a metal material is broken due to hydrogen embrittlement can be narrowed down only to the period from the inspection before the fracture to the inspection after the breakage when the fracture is recognized, and the length of the period is dependent on the inspection interval.

On the other hand, in the present embodiment, the hydrogen embrittlement rate (fracture surface morphology, reduction of area, etc.) obtained from the breakage result of the metal material is used as an index, and the hydrogen embrittlement rate changes depending on the temperature, so that the relational expression F between the hydrogen embrittlement rate and the temperature is derived in advance, and the fracture temperature K is estimated from the hydrogen embrittlement rate of the actually fractured metal material to be estimated using the relational expression F.

Then, the fracture occurrence period T is narrowed down by associating the estimated fracture temperature K with the temperature change under the service environment. In addition, since the higher the load stress is, the more likely it is that fracture will occur due to hydrogen embrittlement. Therefore, outliers that generate high stress are detected from the obtained environmental information, and the fracture occurrence probabilities are ranked in descending order of continuous time. As a result, the timing of when hydrogen embrittlement breakage occurs can be narrowed down to a shorter period.

As a result, the breakage period of the metal material due to hydrogen embrittlement (the service period of the metal material or the structure containing the metal material in the configuration) can be estimated more accurately and can be grasped more accurately. In addition, the metal material or equipment containing the metal material can be efficiently renewed based on the accurately estimated service period information.

The estimation apparatus 1 described in the present embodiment can be realized by a computer including a CPU, a memory, an input/output interface, a communication interface, and the like. It is also possible to create a program for operating a computer as such an apparatus and a storage medium for the program.

REFERENCE SIGNS LIST

1 Estimation apparatus
11 Data acquisition unit
12 Data storage unit
13 Hydrogen embrittlement rate calculation unit
14 Fracture temperature estimation unit
15 Fracture occurrence time narrowing unit
16 Fracture timing estimation unit

The invention claimed is:

1. An estimation method for estimating when a fracture occurred in a metal material to thereby reduce a number of times that the metal material must be checked and to reduce the usage of sensing monitors in order to determine if a fracture has occurred, the method performed by an estimation apparatus, the method comprising:
   (i) receiving input data including image data of a surface of the metal material and temperature information of an installation environment in which the metal material was installed;
   (ii) transforming the image data of the surface of the metal material and the temperature information into a hydrogen embrittlement rate-temperature graph to thereby acquire a relationship between the image data and the temperature information;
   (iii) calculating a fracture temperature of the metal material from a hydrogen embrittlement rate of the metal material based on the relationship between the image data and the temperature information;
   (iv) calculating a period during which the fracture temperature was obtained as a fracture occurrence period of the metal material by using the temperature information;
   (v) calculating a timing of when stress was applied to the metal material during the fracture occurrence period as a timing of when a fracture occurred in the metal material; and
   (vi) renewing the metal material in the installation environment based on the timing of when the fracture occurred in the metal material,
   wherein, in the step (v), outliers of the stress applied during the fracture occurrence period are detected using a predetermined outlier test method, and a period during which outliers are continuously detected is a period when higher stress was applied, and
   wherein, in the step (v), periods during which outliers are continuously detected are ranked in descending order of period length when higher stress was applied, and the timing of when a fracture occurred in the metal material is also ranked according to the ranking of the periods during which outliers are continuously detected.

2. The estimation method according to claim 1, wherein the hydrogen embrittlement rate is a percentage brittle fracture indicating a ratio of a hydrogen embrittlement fracture surface to an entire fracture surface in a fracture surface of the metal material, when a fracture surface including dimples is a ductile fracture surface and a fracture surface other than the fracture surface including dimples is a hydrogen embrittlement fracture surface.

3. The estimation method according to claim 2, wherein, in the step (v), outliers of the stress applied during the fracture occurrence period are detected using a predetermined outlier test method, and a period during which outliers are continuously detected is a period when higher stress was applied.

4. The estimation method according to claim 2, wherein the metal material is a metal material installed outdoors or a metal material contained in a structure installed outdoors, and
   in the step (v), outliers of outdoor wind power loaded during the fracture occurrence period are detected using a predetermined outlier test method, and a period during which outliers are continuously detected is a period when larger wind was applied.

5. The estimation method according to claim 1, wherein the hydrogen embrittlement rate is the ratio of a reduction of area of the metal material which fractured in air to a reduction of area of the metal material which fractured in hydrogen.

6. The estimation method according to claim 5, wherein, in the step (v), outliers of the stress applied during the fracture occurrence period are detected using a predetermined outlier test method, and a period during which outliers are continuously detected is a period when higher stress was applied.

7. The estimation method according to claim 5, wherein the metal material is a metal material installed outdoors or a metal material contained in a structure installed outdoors, and
   in the step (v), outliers of outdoor wind power loaded during the fracture occurrence period are detected using a predetermined outlier test method, and a period during which outliers are continuously detected is a period when larger wind was applied.

8. The estimation method according to claim 1, wherein the metal material is a steel material contained in a concrete structure.

9. An estimation method for estimating when a fracture occurred in a metal material to thereby reduce a number of times that the metal material must be checked and to reduce the usage of sensing monitors in order to determine if a fracture has occurred, the method performed by an estimation apparatus, the method comprising:
   (i) receiving input data including image data of a surface of the metal material and temperature information of an installation environment in which the metal material was installed;
   (ii) transforming the image data of the surface of the metal material and the temperature information into a hydrogen embrittlement rate-temperature graph to thereby acquire a relationship between the image data and the temperature information;
   (iii) calculating a fracture temperature of the metal material from a hydrogen embrittlement rate of the metal material based on the relationship between the image data and the temperature information;
   (iv) calculating a period during which the fracture temperature was obtained as a fracture occurrence period of the metal material by using the temperature information;
   (v) calculating a timing of when stress was applied to the metal material during the fracture occurrence period as a timing of when a fracture occurred in the metal material; and
   (vi) renewing the metal material in the installation environment based on the timing of when the fracture occurred in the metal material, wherein the metal material is a metal material installed outdoors or a metal material contained in a structure installed outdoors, in the step (v), outliers of outdoor wind power loaded during the fracture occurrence period are detected using a predetermined outlier test method, and a period during which outliers are continuously detected is a period when larger wind was applied, and in the step (v), periods during which outliers are continuously detected are ranked in descending order of period length when higher stress was applied.

10. The estimation method according to claim 9, wherein the structure is a concrete pole.

11. The estimation method according to claim 9, wherein the metal material is a steel material contained in a concrete structure.

* * * * *